US007662639B2

(12) United States Patent
Lefebvre-Despeaux et al.

(10) Patent No.: US 7,662,639 B2
(45) Date of Patent: Feb. 16, 2010

(54) COMPOSITION, KIT AND METHOD OF DETECTING AND LOCATING TRACES OF BLOOD

(75) Inventors: Jean-Marc Lefebvre-Despeaux, Monte Carlo (MC); Loïc Blum, Caluire (FR)

(73) Assignee: Roc Import, Monte Carlo (MC)

( * ) Notice: Subject to any disclaimer, the term of this patent is extended or adjusted under 35 U.S.C. 154(b) by 911 days.

(21) Appl. No.: 10/509,326

(22) PCT Filed: Apr. 24, 2003

(86) PCT No.: PCT/FR03/01299

§ 371 (c)(1),
(2), (4) Date: Oct. 6, 2004

(87) PCT Pub. No.: WO03/091687

PCT Pub. Date: Nov. 6, 2003

(65) Prior Publication Data

US 2005/0176082 A1 Aug. 11, 2005

(30) Foreign Application Priority Data

Apr. 25, 2002 (FR) .................................. 02 05230

(51) Int. Cl.
*G01N 21/76* (2006.01)
*G01N 33/48* (2006.01)
*C09K 11/06* (2006.01)

(52) U.S. Cl. ............. 436/166; 252/301.16; 252/301.27; 252/301.28; 422/52; 422/61; 436/2; 436/66; 436/94; 436/172

(58) Field of Classification Search .................. 422/52, 422/61; 436/2, 63, 66, 74, 164, 166, 172; 252/301.16, 301.27–301.28
See application file for complete search history.

(56) References Cited

U.S. PATENT DOCUMENTS

| 3,959,081 | A | * | 5/1976 | Witz et al. ..................... 435/34 |
| 4,176,007 | A | * | 11/1979 | Frosch et al. ................. 435/34 |
| 4,396,579 | A | * | 8/1983 | Schroeder et al. ............. 422/52 |
| 4,900,680 | A | * | 2/1990 | Miyazawa et al. ............ 436/71 |
| 4,977,080 | A | * | 12/1990 | Milbrath ....................... 435/28 |
| 5,279,940 | A | | 1/1994 | Kissel |
| 5,380,650 | A | | 1/1995 | Barnard et al. |
| 5,384,265 | A | * | 1/1995 | Kidwell et al. ............... 436/525 |
| 5,556,758 | A | * | 9/1996 | Allen .......................... 435/7.9 |
| 5,770,116 | A | | 6/1998 | Byrne et al. |
| 5,833,887 | A | | 11/1998 | Byrne et al. |

FOREIGN PATENT DOCUMENTS

| DE | 19633808 | * | 2/1998 |
| JP | 59-77354 | * | 5/1984 |
| JP | 8-51997 | * | 2/1996 |

OTHER PUBLICATIONS

Stross, F. H. et al, Journal of Organic Chemistry 193), 3, 385-404.*
Brabec, F., Collection of Czechoslovak Chemical Communications 1972, 37, 1605-1606.*
Seitz, W. R. et al, Analytical Chemistry 1972, 44, 957-963.*
Yurow, H. W. et al, Analytica Chimica Acta 1975, 77, 324-326.*
Burke, B. A. et al, Journal of Chemical Education 1999, 76, 65-67.*
McGrath, J., British Medical Journal 1942, 156-157.*
Moucka, V. et al, Chemicke Listy pro Vedu a Prumysl 1956, 50, 312-314.*
Ojima, H., Nippon Kagaku Zasshi 1963, 84, 909-913.*
Arima, T., Kagaku Keisatsu Kenkyusho Hokoku 1964, 17, 9-14.*
Gill, P. et al, Electrophoresis 1987, 8, 38-44.*
Jung, J. M. et al, International Journal of Legal Medicine 1991, 104, 145-148.*
Guenther, S. et al, International Journal of Legal Medicine 1995, 108, 154-156.*
Rudbeck, L et al, BioTechniques 1998, 25, 588-90, 592.*
Tsukada, K. et al, Legal Medicine 2002, 4, 239-245.*
Andreasson, H. et al, BioTechniques 2002, 33, 402-404, 407-411.*
E.H. White et al., "Luminol Chemiluminescence", Chemi- and Bioluminescence, ed. by J.G. Burr, Marcel Dekker, Inc., New York, 1985, pp. 215-244.
W. Specht et al., "The Chemiluminescence of Hemin: An Aid for Finding and Recognizing Blood Stains Important for Forensic Purposes", Angewade Chemie, vol. 15, 1937, pp. 155-157.
F. Proescher et al., "Detection of Blood by Means of Chemiluminescence", Journal of Laboratory Clinical Medicine, vol. 24, 1939, pp. 1183-1189.
M. Grodsky et al., "Simplified Preliminary Blood Testing. An Improved Technique and a Comparative Study of Methods", Journal of the America Institute of Criminal Law and Criminology, vol. 42, 1951, pp. 95-104.
K. Weber, "Die Anwedung der Chemiluminescenz des Luminols in der gerichtlichen Medizin und Toxikologie", I. Der Nachweis von Blutspuren, Deutsche Zeitschrift für die gesamte Gerichtliche Medizin, vol. 57, 1966, pp. 410-423.

(Continued)

*Primary Examiner*—Arlen Soderquist
(74) *Attorney, Agent, or Firm*—Greenblum & Bernstein, P.L.C.

(57) ABSTRACT

The invention relates to a composition for the detection of traces of human or animal blood. The aforementioned composition comprises a luminol compound, an oxidizing agent and a base which are diluted in a preferably aqueous solvent. Said composition is characterized in that:
the luminol compound is present in a quantity providing a concentration of between 1 and 20 mmoles/l in the end composition,
the oxidizing agent is hydrogen peroxide which is present at a concentration of between 25 and 100 mmoles/l in the end composition,
the base is soda, NaOH, which is present at a concentration of between 25 mmoles/l and 500 mmoles/l in the end composition.

The invention also relates a kit and a method for preparing said composition. Furthermore, the invention relates to a method of detecting and locating traces of human or animal blood.

10 Claims, No Drawings

OTHER PUBLICATIONS

R.R.J. Grispino, "The Effect of Luminol on the Serological Analysis of Dried Human Bloodstains", Crime Laboratory Digest, vol. 17, No. 1, 1990, pp. 13-23.

Partial English translation of Takayama et al., Chemiluminescence Reactions Used in Crime Scene Investigation, Chemistry and Education , 1966, vol. 44, No. 8, p. 502-505.

Gamoh et al., Academic Research Report by Kochi University, 1997, vol. 46, Natural Science, p. 109-118, "Comparison of Potassium Ferricyanide with Hemoglobin as a Oxidizing Reagent and, Effect of pH Value in Luminol Chemiluminescence Detection of Hydrogen Peroxide".

Plakhotina et al., Prikl Biokhim Mikrobiol. 1974, vol. 10, No. 4, p. 607-610, "Effect of the Reagent Concentration and pH on the Intensity of Luminescence during Protein Estimation by Chemiluminescence".

Takayama et al., Chemiluminescence Reactions Used in Crime Scene Investigation, Chemistry and Education , 1996, vol. 44, No. 8, p. 502-505, 562.

English translation of a paper from the French Defense Department Gendarmerie Nationale Criminal Research Institute Biology Department, The effect of the Blue Star™ blood reagent on DNA.

Paper from the domestic minister of Russia, dated May 3, 2006 having a Cover page and 16 pages, and a partial English translation thereof.

* cited by examiner

COMPOSITION, KIT AND METHOD OF DETECTING AND LOCATING TRACES OF BLOOD

CROSS-REFERENCE TO RELATED APPLICATIONS

The present application is a U.S. National Stage of International Application No. PCT/FR03/01299, filed Apr. 24, 2003, which claims priority under 35 U.S.C. §119 of French Patent Application No. 02/05230, filed Apr. 25, 2002.

BACKGROUND OF THE INVENTION

1. Field of the Invention

The invention pertains to a composition designed for the detection of traces of human or animal blood, including therein a field kit and a procedure for the preparation of the composition in question. The invention further encompasses a procedure for the detection and the localisation of traces of human or animal blood.

The procedure of searching and the localisation of human and animal blood traces by means of chemiluminescence is an already well-established and documented factor.

The luminescence designates the ensemble of emission phenomena of electro-magnetic ultraviolet rays, either visible or in the infra-red range and that are not provoked by a thermal effect.

Certain molecules, the luminophores, possess the property, after they have been brought to an excited state, to emit this so-called <<cold light>> while in the process of returning to their fundamental state. The phenomenon may be provoked by different means and, depending on the nature of the energy source that brings a molecule to its excited state, different types of luminescence can be defined.

Chemiluminescence represents the emission of light produced directly or indirectly by a chemical reaction. In general, chemiluminescent reactions result from the process of oxidation.

For the detection of human or animal blood, the luminol (5-amino-2.3-dihydro-1.4-phthalazinedione) is the most commonly used chemiluminescent compound, although a number of other luminol compounds are equally employed.

In an aqueous solution, the chemiluminescent reaction of luminol requires the presence of a system of oxidisation and an alkaline environment (White E. H. & Roswell, D. F. 1985. Luminol chemiluminescence. *Chemi-and Bioluminescence* (Burr, J. G., ed.), Marcel Dekker, New York, pp. 215-244).

The oxidation of luminol leads to the formation of the ion aminophthalate in an excited state whose return to its fundamental state is accompanied by the emission of light.

The quantum efficiency yield of the reaction is feeble (approximately 0.01) and the emission spectrum presents a maximum at 430 nm (light-blue colour) (White, E. H. & Roswell, D. F. 1985. *Luminol chemiluminescence. Chemi- and Bioluminescence* (Burr, J. G., ed.), Marcel Dekker, New York, pp. 215-244).

The principal compounds that are able to act as catalysts in this light-emitting reaction are the transition metals ($Cr^{3+}$, $Mn^{4+}$, $Fe^{2+}$, $Fe^{3+}$, $CO^{2+}$, $Ni^{2+}$, $Cu^{2+}$, $Hg^{2+}$), free or complexed, hemin and peroxidase (enzyme extracted, for instance, from horse radish).

Hemin is a particular biochemical structure that forms an integral part of peroxidase. This structure is equally present in haemoglobin, which is the carrier protein of oxygen and of part of $CO_2$ in the blood.

Hence, the presence of haemoglobin—thus, of blood—can be made evident by exploiting the ability of hemin to catalyse the chemiluminescence of luminol.

In other words, a mixture of luminol/oxidising agent/alkaline(base) agent, when coming into contact with blood, will emit light.

2. Discussion of Background Information

Already more than 60 years ago, a method to test for the presence of blood by means of this kind of compound was proposed as an empirical aid for detecting traces of blood as an instrument in criminal and forensic investigations.

Thus, in 1937, Specht, W. in *The Chemiluminescence of hemin: an aid for finding and recognizing blood stains important for forensic purposes. Angewande Chemie,* 10, 155-157, was the first to propose demonstrating at the scene of a crime the presence of blood to serve as evidence in criminal and forensic investigations, this by using a compound containing 0.1 part by weight of luminol, 3 parts by weight of an alkaline agent, being sodium carbonate, and 15 parts by weight of an oxidising agent, being hydrogen peroxide 30% diluted in 100 parts by weight of distilled water.

In 1937, Specht, W. in *The Chemiluminescence of hemin: an aid for finding and recognizing blood stains important for forensic purposes. Angewande Chemie,* 10, 155-157, studied and demonstrated the sensitivity of the luminescent reaction with this reactive agent on traces of dried blood, then diluted to 1:2 000 by volume.

In 1939 Proescher, F. & Moody, A. M. in *Detection of blood by means of chemiluminescence. Journal of Laboratory Clinical Medicine.,* 24, 1183-1189, recalled that Specht, W., in 1937, in his article *The Chemiluminescence of hemin: an aid for finding and recognizing blood stains important for forensic purposes. Angewande Chemie,* 10, 155-157, had in tickets and brushwood conducted tests on blood exposed to the sun and to the rain and that, under these varying conditions, the chemiluminescent reaction had occurred.

As to their own efforts, they tested the compound of Specht, W., expounded in 1937 in *The Chemiluminescence of hemin: an aid for finding and recognizing blood stains important for forensic purposes. Angewande Chemie,* 10, 155-157, both on the blood from animals and humans up to dilutions of 1:1 000 000 and demonstrated thereby that the chemiluminescent reaction occurred on both occasions.

In 1951, Grodsky, M., Wright, K. & Kirk, P. L., in *Simplified preliminary blood testing. An improved technique and comparative study of methods. Journal of the America Institute of Criminal Law and Criminology,* 42, 95-104, noting that the sensitivity and the reactivity of luminol are very difficult to control while the hydrogen peroxide is being used in the capacity of oxidising agent, proposed the use of a perborate oxidising agent. He likewise proposed a field kit consisting of different receptacles each independently containing the said luminol, the perborate oxidising agent, and the alkaline agent sodium carbonate. This field kit would also hold accessories such as plastic and glass vaporisers, filter paper, a bottle of distilled water, a flashlight to allow for the mixing of the reactive agents in the dark, plus plastic receptacles to hold and carry along the traces of blood or other minute bits of evidence.

In that respect, Grodsky, M., Wright, K. & Kirk, P. L. in 1951, in the article *Simplified preliminary blood testing. An improved technique and comparative study of methods. Journal of the America Institute of Criminal Law and Criminology,* 42, 95-104, managed to optimise the chemiluminescent reaction of luminol, in the presence of very diluted blood, being a dilution of 1:5 000 000 by volume.

In 1939, Proescher, F. & Moody, A. M. in *Detection of blood by means of chemiluminescence. Journal of Laboratory Clinical Medicine.*, 24, 1183-1189, just like Grodsky, M., Wright, K. & Kirk, P. L. in 1951 in *Simplified preliminary blood testing. An improved technique and comparative study of methods. Journal of the America Institute of Criminal Law and Criminology*, 42, 95-104, recommended to first spray the location with hydrochloric acid in order to decompose the haemoglobin and to improve the sensitivity level of the test.

In 1966, Weber, K. in *Die Anweldung der Chemiluminescenz des Luminols in der Gerichtlichen Medizin und Toxicologie. I. Der Nachweis von Blutspuren. Deutsche Zeitschrift für die gesamte Gerichtliche Medizin*, 57, 410-423, provided evidence of the fact that the use of a carbonate alkaline agent did merely provoke a slow reaction of haemoglobin oxidation and that, consequently, the luminescence was much weaker when such a carbonate alkaline agent was utilised. Therefore, he advocated the use of sodium hydroxide for an alkaline agent. In 1966, Weber, K. in *Die Anweldung der Chemiluminescenz des Luminols in der Gerichtlichen Medizin und Toxicologie. I. Der Nachweis von Blutspuren. Deutsche Zeitschrift für die gesamte Gerichtliche Medizin*, 57, 410-423, in his turn noted that the concentrations with luminol and hydrogen peroxide used in the reagents by Specht, W. in 1937 in *The Chemiluminescence of hemin: an aid for finding and recognizing blood stains important for forensic purposes. Angewande Chemie*, 10, 155-157, were too strong and provoked a concentration inhibition in the reaction of luminol linked to the concentration of the reagents and hence a disappearance of the chemiluminescence and a notable lowering in the evidence of blood traces. In 1966, Weber, K. in *Die Anweldung der Chemiluminescenz des Luminols in der Gerichtlichen Medizin und Toxicologie. I. Der Nachweis von Blutspuren. Deutsche Zeitschrift für die gesamte Gerichtliche Medizin*, 57, 410-423, thus proposed a composition consisting of 0.4 mmoles/l de luminol, 17.6 mmoles/l of hydrogen peroxide, and 45 mmoles/l of sodium hydroxide or potassium hydroxide, diluted in distilled water, for the detection of traces of dried or fresh blood up to a dilution ratio of 1:20 000 000.

In 1990, Grispino, R. R. J. in *The effects of luminol on serological analysis of dried bloodstains Crime Laboratory Digest*, 17 (1), 13-23, proposed using a luminol composition containing 5.6 mmoles/l of luminol, 472 mmoles/l of potassium or sodium carbonate and 100 mmoles/l of hydrogen peroxide $H_2O_2$, diluted in distilled water, for the detection of traces of blood dried during several days and of fresh blood in dilutions of this blood from 1:10 000 up to 1:100 000.

All of the above demonstrates that, for the purpose of detecting traces of blood at the scene of a crime, the use of a composition containing luminol in combination with an alkaline agent and an oxidising agent dates back a long way in the past.

With reference to this particular application, it is advocated to use hydrogen peroxide as an oxidising agent rather than sodium perborate, as sodium perborate is not readily soluble in water and impedes the vaporisation arrangement of the composition. Likewise, the use of sodium hydroxide or potassium hydroxide as an alkaline agent is advocated rather than a composition of carbonate, for the oxidation reaction of luminol was much slower with a carbonate compound than with a hydroxide one, meaning that the light emission was less intense with the former compound.

In 1966, Weber, K. in the article *Die Anweldung der Chemiluminescenz des Luminols in der Gerichtlichen Medizin und Toxicologie. I. Der Nachweis von Blutspuren. Deutsche Zeitschrift für die gesamte Gerichtliche Medizin*, 57, 410-423, thus proposed a composition of this type but containing rather weak quantities of luminol and of hydrogen peroxide, as too strong quantities of these compounds bring with them an inhibition in the luminol reaction and, consequently, a disappearance of the chemiluminescence and a notable lowering of the evidence of traces of blood.

Furthermore, Byrne, in the patents U.S. Pat. Nos. 5,770,116 and 5,833,887, has proposed the use of the chemiluminescent reaction of luminol in order to detect traces of blood loss in wounded game animals, on the hunting sites, in conditions of failing light and reduced visibility.

To this effect, Byrne, in the patents U.S. Pat. Nos. 5,770,116 and 5,833,887, advocates the use of a composition containing, in addition to luminol, sodium perborate for an oxidising agent and sodium carbonate as an alkaline agent.

Nevertheless, this composition presents difficulties linked to the utilisation of the sodium perborate and the sodium carbonate as already described supra.

This is particularly inhibiting for an application to be used on the occasion of the hunt, specifically when blood detection is sought not in the dead of (black) night but rather under the simple conditions of failing light, as is the case at the time of sundown, when the loss of luminous intensity emitted by the luminol reaction with the blood is particularly bothersome since this luminescent intensity at such a time may not be sufficiently noticeable for the hunter to detect the traces of blood left by his prey.

Moreover, all tests carried out in the past were conducted on much diluted blood samples.

SUMMARY OF THE INVENTION

The invention provides a composition for the detection of traces of human or animal blood comprising:
- a luminol compound present in a concentration of between 1 and 20 mmoles/l in the end composition,
- an oxidizing agent comprising hydrogen peroxide present in a concentration of between 25 and 100 mmoles/l in the end composition,
- a base comprising NaOH present in a concentration of between 25 mmoles/l and 500 mmoles/l in the end composition, and
- a solvent.

Another aspect of the invention provides a composition wherein the luminol compound comprises at least one of luminol, diethyl isoluminol, and aminobutylethyl isoluminol.

Yet another aspect of the invention provides a composition wherein the NaOH is present in a concentration of between 25 and 150 mmoles/l in the end composition.

A further aspect of the invention provides a composition wherein the NaOH is present in a concentration of between 25 and about 90 mmoles/l in the end composition.

Another aspect of the invention provides a composition wherein the solvent is non-carbonated water.

Yet another aspect of the invention provides a method of detection comprising, applying the above composition to a surface to detect traces of human or animal blood.

A further aspect of the invention provides a method of detection comprising, applying the above composition to a surface to detect traces of animal blood on hunting grounds.

Another aspect of the invention provides a method of detection comprising, applying the above composition to a surface to detect traces of human blood at the scene of a crime or accident.

Yet another aspect of the invention provides a field kit for the preparation of the above composition wherein the kit comprises:

a first receptacle including at least an individual dosage of luminol compound in a quantity ranging between 1 and 20 mmoles;
a second receptacle includes at least an individual dosage containing between 25 and 100 mmoles of hydrogen peroxide, and
a third receptacle including at least an individual dosage containing between 25 and 500 mmoles of NaOH.

A further aspect of the invention provides a field kit wherein:
the first receptacle includes at least an individual dosage containing a luminol compound in a supply quantity of 1 to 10 mmoles of luminol,
the second receptacle includes at least an individual dosage containing between 25 and 100 mmoles of hydrogen peroxide, and
the third receptacle includes at least an individual dosage containing between 25 and 150 mmoles of soda, NaOH.

Another aspect of the invention provides a field kit wherein:
the first receptacle includes at least an individual dosage containing a luminol compound in a quantity of approximately 5 mmoles,
the second receptacle includes at least an individual dosage containing approximately 50 mmoles of hydrogen peroxide, and
the third receptacle includes at least an individual dosage containing between 25 and 50 mmoles of NaOH.

Yet another aspect of the invention provides a field kit for the preparation of the above composition wherein the kit comprises:
a first receptacle including at least an individual dosage comprising the luminol compound in a quantity of between 1 and 20 mmoles in a pre-mixture with either NaOH, in a quantity of between 25 and 500 mmoles, or with 25 to 100 mmoles of hydrogen peroxide, in a solid compatible form; and
a second receptacle including at least an individual dosage comprising between 25 and 100 mmoles of hydrogen peroxide, or between 25 and 500 mmoles of NaOH, corresponding to the pre-mixture in the first receptacle.

A further aspect of the invention provides a field kit for the preparation of the above composition wherein the kit comprises:
a first receptacle including at least an individual dosage containing the luminol compound in a quantity sufficient to provide approximately 5 mmoles in a pre-mixture with either 25 to 150 mmoles of NaOH, or 50 mmoles of hydrogen peroxide, in a solid compatible form, and
a second receptacle including at least an individual dosage containing 50 mmoles of hydrogen peroxide, or between 25 and 150 mmoles of NaOH, in accordance with the pre-mixture in the first receptacle.

Another aspect of the invention provides a field kit for the preparation of the above composition wherein the kit comprises:
a first receptacle including at least an individual dosage containing the luminol compound in a quantity sufficient to provide approximately 5 mmoles in a mixture with either 25 to 50 mmoles, or 90 mmoles of NaOH, or 50 mmoles of hydrogen peroxide, in a solid compatible form, and
a second receptacle including at least an individual dosage containing either 50 mmoles of hydrogen peroxide, or between 25 and 50 mmoles, or 90 mmoles of NaOH.

Yet another aspect of the invention provides a field kit wherein each receptacle comprises a resealable receptacle made of plastic material or glass.

A further aspect of the invention provides a field kit wherein at least one receptacle is formed by an alveolus fitted inside at least one blister pack.

Another aspect of the invention provides a field kit for the preparation of the above composition wherein the field kit contains at least one blister pack with a minimum of three alveoli, wherein at least one alveoli contains an individual dosage holding the luminol compound in a quantity sufficient to provide between 1 and 20 mmoles, and wherein at least one other alveoli contains an individual dosage holding between 25 and 500 mmoles of NaOH, and wherein at least one other alveoli contains an individual dosage holding between 25 and 100 mmoles of hydrogen peroxide.

Yet another aspect of the invention provides a field kit for the preparation of the above composition wherein the field kit contains either a blister pack and at least two alveoli, wherein at least one alveoli contains an individual dosage of the luminol compound in a quantity sufficient to provide between 1 and 20 mmoles in a pre-mixture with either NaOH, in a quantity of between 25 and 500 mmoles, or with 25 to 100 mmoles of hydrogen peroxide in solid compatible form; and at least one other alveoli contains an individual dosage with either a quantity of between 25 and 100 mmoles of hydrogen peroxide, or of 25 to 500 mmoles of NaOH depending on the first pre-mixture; or at least one blister pack containing at least one alveolus with a pre-mixture of the above-mentioned three basic components.

A further aspect of the invention provides a field kit wherein at least one of the individual dosages is in the form of a pill.

Another aspect of the invention provides a field kit wherein every one of the individual dosages is in the form of a pill.

Yet another aspect of the invention provides a field kit wherein the individual dosage further contains excipients to facilitate direct crushing of the pill thereby avoiding formation of moist granulation due to the presence of NaGH, and wherein the individual dosages also contain excipients that will facilitate the disintegration of the pill.

A further aspect of the invention provides a field kit wherein the luminol compound comprises luminol.

Another aspect of the invention provides a field kit for the preparation of the above composition comprising: a luminol, an oxidizing agent, and a base have been formulated in a single pre-mixture in formulations that allow their compatibility without generating a premature reaction, thus making it possible to enclose them jointly in one single receptacle.

Yet another aspect of the invention provides a method of making a reconstitution of the above composition wherein the reconstitution comprises diluting in water an individual dosage of a luminol compound, an individual dosage of NaOH, or an individual dosage of a mixture of a luminol compound and NaOH, and an individual dosage of hydrogen peroxide.

A further aspect of the invention provides a method of search and localization of a wounded or struck down animal wherein the above composition is vaporized on the areas of terrain where the animal is assumed to have passed, thereby producing a luminous reaction through the contact of the composition with blood traces left behind by the animal.

Another aspect of the invention provides a method of search and localization of traces of human blood at the scene of a crime or of an accident in conditions of reduced visibility, wherein the above composition is vaporized on the mentioned scene, thereby producing a luminous reaction through the contact of the composition with the traces of human blood.

Yet another aspect of the invention provides a method of search and localization of traces of human blood at the scene of a crime, wherein the individual dosages are mixed together and applied to the scene thereby producing a luminous reaction through the contact of the composition with the traces of human blood.

A further aspect of the invention provides a field kit wherein the excipient to facilitate the direct crushing of the pill comprises at least one of lactose, cellulose, and calcium phosphate; and the excipient that facilitates disintegration of the pill comprises at least one of croscarmellose and sodium starch glycolate.

Another aspect of the invention provides a method of making a reconstitution of the above composition wherein the individual doses are taken from receptacles of a kit.

Yet another aspect of the invention provides a method of search and localization of a wounded or struck down animal, wherein the above composition is obtained by diluting in water an individual dosage of a luminol compound, an individual dosage of NaGH, or an individual dosage of a mixture of a luminol compound and NaOH, and an individual dosage of hydrogen peroxide.

A further aspect of the invention provides a method of search and localization of traces of human blood wherein the method is conducted in conditions of reduced visibility.

Another aspect of the invention provides a method of search and localization of traces of human blood at the scene of a crime or of an accident in conditions of reduced visibility, comprising vaporizing the reconstitution of the above composition on the mentioned scene, thereby producing a luminous reaction through the contact of the composition with the traces of human blood.

Yet another aspect of the invention provides a field kit as wherein all of the receptacles are formed by an alveolus fitted inside at least one blister pack.

The present invention aims at reducing the inconveniences that attach to the compositions that have been the subjects of tests in the past, introducing to the process a method that can be employed under real practical conditions and circumstances, that is to say a process that will allow the revelation of even minute traces of pure blood, instantly and with a luminosity of sufficient intensity to be visible, not only in total darkness but also under conditions of fading and just failing light that corresponds to the diffused light at sundown.

To this end, the invention proposes a composition for the detection of traces of human or animal blood of the type comprised of a compound of luminol, an oxidising agent, and a base, diluted in, preferably, an aqueous solvent, with the specification that the luminol compound be present in a quantity providing a concentration of between 1 and 20 mmoles/l in the end composition, that the oxidizing agent be hydrogen peroxide which is present in a concentration of between 25 and 100 mmoles/l in the end composition, and that the base be soda, NaOH, which is present in a concentration of between 25 mmoles/l and 500 mmoles/l in the end composition.

DETAILED DESCRIPTION OF THE INVENTION

In order that the application of the formula be realised at its most advantageous consequence, the luminol compound is present in a quantity allowing for a concentration between 1 and 10, preferably of the order of 5 mmoles/l.

Furthermore, it shall be advantageous for numerous applications to limit the volume of soda, NaOH, from 25 to 150 mmoles/l.

It is preferable that the pH of the composition be kept below approximately 11.5, as it will be explained a little further on.

It will, of course, be quite understandable to the expert in the field that the concentration of each of the components be fixed in function of the concentration of the other components used.

Likewise, the designation "luminol compound" as used in the description and in the establishment of the subject claims signifies the luminol and every precursor compound or compound derived from luminol, for example, formulated through the substitution of luminol by at least one substituting component such as alkyl, notably methyl, amine, hydroxyl, etcetera, and capable of producing a chemiluminescence of the type produced by luminol. Examples of such compounds are diethyl isoluminol and aminobutylethyl isoluminol.

Preferably, however, the luminol compound is to be made up of luminol.

In the preferred first preparation, soda, NaOH, is present in a concentration of approximately 90 mmoles/l in the end composition.

In the secondary preparation of choice, soda, NaOH, is present in a concentration of from 25 to 50 mmoles/l in the end composition.

In all cases, preferably, the aqueous solvent should be water, and, for the best results, non-carbonated water.

The other purpose of the invention is the utilisation of the composition to detect traces of human or animal blood.

The composition as prescribed in the first preparation is particularly appropriate to detect traces of animal blood during the hunt.

The composition as prescribed in the second preparation is particularly appropriate for detecting traces of human blood at the scene of a crime or at the scene of an accident.

The invention likewise introduces a field kit designed for the preparation of its composition which, in its first preferable formulation, shall consist of:

- in a first receptacle at least an individual dosage containing a luminol compound in a quantity ranging from 1 to 20 mmoles,
- in a second receptacle at least an individual dosage containing from 25 to 100 mmoles of hydrogen peroxide, and
- in a third receptacle at least an individual dosage containing from 25 to 500 mmoles of soda, NaOH.

In a first variant, this first selected formulation for the invention's kit is adapted for the preparation of the composition in accordance with the first preparation and consists of:

- in a first receptacle, at least an individual dosage containing the said luminol compound in particular in a quantity ranging from 1 to 10 mmoles,
- in a second receptacle at least an individual dosage containing from 25 to 100 mmoles of hydrogen peroxide, and
- in a third receptacle at least an individual dosage containing from 25 to 150 mmoles of soda, NaOH.

In a second variant, this first preferable formulation of the kit has been adapted for the preparation of the composition in keeping with the second mode of realisation, particularly for the use of it at the scene of a crime, and it contains:

- in a first receptacle at least an individual dosage containing a luminol compound in a quantity of approximately 5 mmoles,
- in a second receptacle at least an individual dosage containing approximately 50 mmoles of hydrogen peroxide, and
- in a third receptacle at least an individual dosage containing from 25 to 50 mmoles of soda, NaOH.

In the second preferred formulation, the kit for the preparation of the composition in keeping with the invention's specifications consists of:
  in a first receptacle at least an individual dosage containing the said luminol compound in a quantity ranging from 1 to 20 mmoles in a pre-mix with either soda, NaOH, and a quantity consisting of between 25 and 500 mmoles, or with 25 to 100 mmoles of hydrogen peroxide in a compatible solid form,
  in a second receptacle, at least an individual dosage containing from 25 to 100 mmoles of hydrogen peroxide, or from 25 to 500 mmoles of soda, in keeping with the pre-mixture of the first receptacle.

Preferably, this kit for the preparation of a composition in keeping with the invention's specifications consists of:
  in a first receptacle at least an individual dosage containing a luminol compound in a quantity ranging from 1 to 20 mmoles of the pre-mix luminol compound with either from 25 to 150 mmoles of soda, NaOH, or with 25 to 100 mmoles of hydrogen peroxide, in a compatible solid form, and
  in a second receptacle at least an individual dosage containing 50 mmoles of hydrogen peroxide, or 25 to 150 mmoles of soda, NaOH, in keeping with the pre-mixture of the first receptacle.

It should be noted that the hydrogen peroxide in a solid form is available on the market, particularly from SIGMA-ALDRICH, either in pills or powder, in the form of an adduct with urea, called "Urea Adduct".

Alternatively, this kit contains:
  in a first receptacle at least an individual dosage containing a luminol compound in a quantity of 5 mmoles of pre-mix luminol, either with from 25 to 50 mmoles, or 90 mmoles, of soda, NaOH, or with 50 mmoles of hydrogen peroxide in compatible solid form, and
  in a second receptacle at least an individual dosage containing either 50 mmoles of hydrogen peroxide, or from 25 to 50 mmoles, or 90 mmoles, of soda, NaOH, in function of the pre-mixture.

In keeping with still another advantageous mode of the invention, the invention's three principal components can be formulated in a single pre-mixture in formulations quite familiar to experts in the art of formulations, allowing their compatibility without premature reaction in order that they can thus be jointly included in a single receptacle. Hence, it is a well-known fact that certain enveloping techniques prevent premature reactions. Thus, the invention equally concerns a formulation in which the three basic components of the invention are combined within a single receptacle.

In all cases, in the invention's kit, each receptacle is by preference a resealable unit made of plastic material or of glass.

These receptacles may also be pouches containing individual dosages in powder form.

More preferable, at least one—or every receptacle—should be formed by an alveolus fitted inside at least one blister pack.

And still more preferable, the invention kit can contain at least one blister pack with at least three alveoli, one of these three containing an individual dosage of the luminol compound in a quantity ranging from 1 to 20 mmoles, another one of these containing an individual dosage from 25 to 500 mmoles of soda, NaOH, and the third one of these alveoli containing from 25 to 100 mmoles of hydrogen peroxide.

Alternatively, the invention kit can contain at least one blister pack with two alveoli as a minimum, one of these containing an individual dosage with a luminol compound in a quantity ranging from 1 to 20 mmoles in a pre-mixture with either soda, NaOHm in a quantity from 25 to 500 mmoles, or from 25 to 100 mmoles of hydrogen peroxide in a compatible and solid form, and the other of these two alveoli containing an individual dosage with either from 25 to 100 mmoles of hydrogen peroxide or from 25 to 500 mmoles of soda, depending on the pre-mixture of the first alveolus.

In a third variant, the kit can hold at least one blister pack and at least one alveolus containing an individual dosage of a pre-mix formulation in the compatible and solid form of the invention's three basic components.

Preferably, in all the variant forms of the invention's kit, at least one of the individual dosages comes in the form of a pill.

Even more preferable, in the invention's kit, each dosage of luminol, hydrogen peroxide, and soda, comes in the form of a pill.

In all of the cases in question, as a useful application, each individual dosage further contains excipients to facilitate the direct crushing and break-up of the pill.

The invention further proposes a procedure of reconstitution of the composition in question, consisting of dilution in water of an individual dosage of luminol compound, an individual dosage of hydrogen peroxide, and an individual dosage of soda, each one of these individual dosages having been taken from the receptacles of the invention's kit.

The invention also proposes a procedure of search and localisation of an animal either wounded or struck down under conditions of reduced visibility, or in the total absence of any light, this procedure being characterised by the vaporisation of the composition as described in the invention or of the composition obtained in accordance with the procedure of reconstitution as described in the invention, such vaporisation to be carried out in areas where the animal is suspected to have passed, in order to produce a luminescent reaction through the contact of the composition with the traces of blood lost by the hunted animal.

Likewise, another objective of the invention is a procedure of search and localisation of traces of blood at the scene of a crime, characterised by the vaporisation of the composition as described in the invention or of the composition obtained in accordance with the procedure of reconstitution as described in the invention, such vaporisation to be carried out at the scene of a crime, in order to produce a luminescent reaction through the contact of the composition with the traces of human blood.

The invention shall become more comprehensible, and its other objectives, details, and advantages shall be made more evident by the text of the explanatory description that follows.

As explained in the invention, one has discovered in a surprising manner that a composition of 1 to 20 mmoles/l of the luminol compound, of 25 to 100 mmoles/l of hydrogen peroxide ($H_2O_2$) acting as an oxidising agent, and of between 25 mmoles/l and 500 mmoles/l of soda (NaOH) as an alkaline agent, diluted in, preferably, an aqueous solvent, allows the rapid and effective discovery of blood traces, either human or animal, fresh or dried, washed or not.

In this composition it is indeed remarkable that a concentration of the luminol compound from 1 to 20 mmoles, preferably from 1 to 10 mmoles/l, will make it possible to obtain a optimal light intensity, without the need to use heavy dosages of the luminol compound.

In fact, using from 25 to 500 mmoles, and to greater advantage from 25 to 150 mmoles, and better with approximately 90 mmoles/l in the end composition of sodium hydroxide, NaOH, and from 25 to 100 mmoles/l of hydrogen peroxide, $H_2O_2$, the luminescent intensity increases with the concentration of the luminol compound, but practically reaches a level plateau starting from 10 to 20 mmoles/l of luminol compound. Nonetheless, according to the specifications of the invention, it is unexpected that with a weak concentration, in particular of approximately 5 mmoles/l of the luminol compound, 93% of the maximal light intensity should be obtained.

The choice for the oxidising agent has fallen on hydrogen peroxide, $H_2O_2$, not only because of its ready availability at an affordable price, but also due to the argument as stated by Grispino, R. R. J. in *The effects of luminol on serological analysis of dried blood stains Crime Laboratory Digest*, 17 (1), 13-23, that the utilisation of a perborate oxidizing agent, which is not readily soluble in water or in an aqueous solvent, brings about a blockage of the vaporisation system of the solution and is consequently not practical for use.

Moreover, it became evident in a surprising manner that it is with hydrogen peroxide that the highest levels of luminosity can be obtained.

In order that the invention may become better understood, several modes of implementation will now be described, using examples for purely illustrative reasons and which are not exhaustive or limiting. Examples 1 to 4 are part of the invention and belong as such to the claim's subject matter. Other examples of the invention providing equivalent results are:

a composition containing from 10 to 20 mmoles/l of the luminol compound, approximately 40 mmoles of NaOH, and approximately 50 mmoles of $H_2O_2$.

a composition containing approximately 5 mmoles/l of the luminol compound, 50 mmoles/l of $H_2O_2$, and approximately 120 mmoles/l of NaOH.

EXAMPLES

Example 1 According to the Invention's Specifications

A composition was prepared according to the invention's specifications, comprised of 5 mmoles/l of luminol, 50 mmoles/l of NaOH, and 50 mmoles/l of $H_2O_2$, diluted in 1 liter of distilled water.

This composition was sprayed on:

sheep's blood diluted in a 1:1 000 000 ratio, and on sheep's blood diluted in a 1:100 000 ratio, pure and fresh sheep's blood, and pure dried sheep's blood.

The composition's pH was measured. The light intensities obtained during the reactions between the composition in question and each of the different samples were measured according to the following protocols.

With respect to the diluted blood, the measure of light intensity was obtained by means of a luminosity meter LUMAC, model Biocounter M2500, manufactured and marketed by the LUMAC corporation. This device was modified so it could be fitted with a photomultiplicator tube HAMAMATSU and linked to its recorder which records the light intensity in an arbitrary unit, following the common practice of specialists in luminometry.

With respect to the measurement of light intensity on the pure fresh blood or the pure dried blood, a camera CCD made by FUJIFILM, model LAS-1000 was used, linked to a computer equipped with a software processor for the automatic recording of peak intensity as well as the length of the reaction time.

The reaction times between the composition as per the invention's specifications and each one of the different blood samples were measured in accordance with the following protocol.

The completion of the reaction is measured by following the curve of the light intensity registered for the diluted blood by the recorder linked to the luminometer when the maximum peak of light intensity is reached; or, conversely, one can take the value given by the computer in the case of the pure blood sample. As one can observe from table 1, in the case of the present example 1 of the invention, on the pure fresh blood and the pure dried blood, the peak of maximum intensity is reached 40 seconds after the moment of vaporisation of the composition.

The results of these measurements are summarised in table 1 below.

Example 2 According to the Invention's Specifications

A composition in accordance with the invention's specifications was prepared, comprised of 5 mmoles/l of luminol, 90 mmoles/l of NaOH, and 50 mmoles/l of $H_2O_2$, diluted in 1 liter of distilled water.

The same measurements as indicated in example 1 were carried out, following identical protocols.

The results of these measurements are summarised in table 1 below.

Example 3 According to the Invention's Specifications

A composition in accordance with the invention's specifications was prepared, comprised of 5 mmoles/l of luminol, 25 mmoles/l of NaOH, and 50 mmoles/l of $H_2O_2$, diluted in 1 liter of distilled water.

The same measurements as indicated in example 1 were carried out, following identical protocols.

The results of these measurements are summarised in table 1 below.

Example 4 According to the Invention's Specifications

A composition in accordance with the invention's specifications was prepared, comprised of 5 mmoles/l of luminol, 40 mmoles/l of NaOH, and 50 mmoles/l of $H_2O_2$, diluted in 1 liter of distilled water.

The same measurements as indicated in example 1 were carried out, following identical protocols.

The results of these measurements are summarised in table 1 below.

Comparative Example 1

By way of comparison, a composition was prepared comprised of 5 mmoles/l of luminol, 10 mmoles/l of NaOH, and 50 mmoles/l of $H_2O_2$, diluted in 1 liter of distilled water.

The same measurements as indicated in example 1 were carried out, following identical protocols.

The results of these measurements are summarised in table 1 below.

Comparative Example 2

A composition as constituted in the past and described by Grispino, R. R. J. in the article *The effects of luminol on* serological analysis of dried blood stains *Crime Laboratory Digest*, 17 (1), 13-23, was prepared. This composition contains 5.6 mmoles/l of luminol, 472 mmoles/l of $Na_2CO_3$, and 100 mmoles/l of $H_2O_2$, diluted in 1 liter of distilled water.

The same measurements as indicated in example 1 were carried out, following identical protocols.

The results of these measurements are summarised in table 1 below.

Comparative Example 3

A composition comprised of the same concentrations of luminol, $H_2O_2$, and an alkaline agent as in the composition of example 2 described by Grispino, R. R. J. in the article *The effects of luminol on serological analysis of dried blood stains Crime Laboratory Digest*, 17 (1), 13-23, was prepared.

However, in this composition, the alkaline agent is $K_2CO_3$ instead of $Na_2CO_3$.

The same measurements as those described for example 1 were carried out with this composition, but using $K_2CO_3$ for the alkaline agent.

The results of these measurements are summarised in table 1 below.

Comparative Example 4

A composition was prepared such as was described by Grodsky, M., Wright, K. & Kirk, P. L. in the article *Simplified preliminary blood testing. An improved technique and comparative study of methods. Journal of the America Institute of Criminal Law and Criminology*, 42, 95-104, and Byrne in the patents U.S. Pat. Nos. 5,770,116 and 5,833,887. This composition contains 5.6 mmoles/l of luminol, 472 mmoles/l of $Na_2CO_3$, and, as an oxidising agent 45.5 mmoles/l of $NaBo_3$.

The same measurements as indicated in example 1 were carried out, following identical protocols.

The results of these measurements are summarised in table 1 below.

Comparative Example 5

A composition as described by Weber, K. in 1966 in the article *Die Anweldung der Chemiluminescenz des Luminols in der Gerichtlichen Medizin und Toxicologie. I. Der Nachweis von Blutspuren. Deutsche Zeitschrift für die gesamte Gerichtliche Medizin*, 57, 410-423. This composition is made up of 0.4 mmoles/l of luminol, 45 mmoles/l of NaOH, and 17.6 mmoles/l of $H_2O_2$, diluted in 1 liter of distilled water.

The same measurements as indicated in example 1 were carried out, following identical protocols.

The results of these measurements are summarised in table 1 below.

Comparative Example 6

A composition was made up of 0.4 mmoles/l of luminol, 45 mmoles/l of KOH, and 17.6 mmoles/l of $H_2O_2$, diluted in one liter of distilled water.

This composition corresponds to the composition described by Weber, K. in 1966 in the article *Die Anweldung der Chemiluminescenz des Luminols in der Gerichtlichen Medizin und Toxicologie. I. Der Nachweis von Blutspuren. Deutsche Zeitschrift für die gesamte Gerichtliche Medizin*, 57, 410-423, according to the specifications for comparative example 5 but in which soda was replaced by potassium hydroxide.

The same measurements as indicated in example 1 were carried out, following identical protocols.

The results of these measurements are summarised in table 1 below.

TABLE 1

| Composition | pH | Blood diluted to 1:1 000 000 | Blood diluted to 1:100 000 | Pure blood - fresh | Pure blood - dried |
| --- | --- | --- | --- | --- | --- |
| Sample 1 as per specification Luminol 5 mmoles/L NaOH 50 mmoles/L $H_2O_2$ 50 mmoles/L | 11.78 | I: 75 u.a. Reaction time: 4 min | I: 1106 u.a. Reaction time: 4 min | I: 66430 u.a./mm$^2$ Reaction time: 40 sec | I: 48405 u.a./mm$^2$ Reaction time: 40 sec |
| Sample 2 as per specification Luminol 5 mmoles/L NaOH 90 mmoles/L $H_2O_2$ 50 mmoles/L | 12.36 | I: 394 u.a. Reaction time: 2 min | I: = saturation | I: 72043 u.a./mm$^2$ Reaction time: 40 sec | I: 73805 u.a./mm$^2$ Reaction time: 1 min |
| Sample 3 as per specification Luminol 5 mmoles/L NaOH 25 mmoles/L $H_2O_2$ 50 mmoles/L | 11.12 | I: 15 u.a. Reaction time: 4 min | I: 123 u.a. Reaction time: 4 min | I: 37445 u.a./mm$^2$ Reaction time: 30 sec | I: 39733 u.a./mm$^2$ Reaction time: 30 sec |
| Sample 4 as per specification Luminol 5 mmoles/L NaOH 40 mmoles/L $H_2O_2$ 50 mmoles/L | 11.5 | I: non-tested Reaction time: non-tested | I: non-tested Reaction time: non-tested | I: 55165 u.a./mm$^2$ Reaction time: | I: 44930 u.a./mm$^2$ Reaction time: |
| Comparative sample 1 Luminol 5 mmoles/L NaOH 10 mmoles/L $H_2O_2$ 50 mmoles/L | 10.21 | I: 4 u.a. Reaction time: 4 min | I: 24 u.a. Reaction time: 4 min | I: 19480 u.a./mm$^2$ Reaction time: 30 sec | I: 17970 u.a./mm$^2$ Reaction time: 20 sec |
| Comparative sample 2 Luminol 5.6 mmoles/L $Na_2CO_3$ 472 mmoles/L $H_2O_2$ 100 mmoles/L | 10.72 | I: 96 u.a. Reaction time: >15 min | I: 250 u.a. Reaction time: 4 min | I: 31235 u.a./mm$^2$ Reaction time: 50 sec | I: 30973 u.a./mm$^2$ Reaction time: 40 sec |

TABLE 1-continued

| Composition | pH | Blood diluted to 1:1 000 000 | Blood diluted to 1:100 000 | Pure blood - fresh | Pure blood - dried |
|---|---|---|---|---|---|
| Comparative sample 3<br>Luminol 5.6 mmoles/L<br>$K_2CO_3$ 472 mmoles/L<br>$H_2O_2$ 100 mmoles/L | 10.95 | I: 30 u.a.<br>Reaction time:<br>>15 min | I: 173 u.a.<br>Reaction time:<br>4 min | I: 33360 u.a./mm$^2$<br>Reaction time:<br>40 sec | I: 26405 u.a./mm$^2$<br>Reaction time:<br>30 sec |
| Comparative sample 4<br>Luminol 5.6 mmoles/L<br>$Na_2CO_3$ 472 mmoles/L<br>$NaBo_3$ 45.5 mmoles/L | 10.90 | I: 155 u.a.<br>Reaction time:<br>>15 min | I: 529 u.a.<br>Reaction time: 4 min | I: 31803 u.a./mm$^2$<br>Reaction time:<br>30 sec | I: 32175 u.a./mm$^2$<br>Reaction time:<br>30 sec |
| Comparative sample 5<br>Luminol 0.4 mmoles/L<br>NaOH 45 mmoles/L<br>$H_2O_2$ 17.6 mmoles/L | 12.33 | I: 245 u.a.<br>Reaction time:<br>8 min | I: 1542 u.a.<br>Reaction time:<br>>15 min | I: 31210 u.a./mm$^2$<br>Reaction time: 20 sec | I: 29853 u.a./mm$^2$<br>Reaction time:<br>20 sec |
| Comparative sample 6<br>Luminol 0.4 mmoles/L<br>KOH 45 mmoles/L<br>$H_2O_2$ 17.6 mmoles/L | 11.86 | I: 255 u.a.<br>Reaction time:<br>4 min | I: 1402 u.a.<br>Reaction time:<br>10 min | I: 29020 u.a./mm$^2$<br>Reaction time:<br>20 sec | I: 27645 u.a./mm$^2$<br>Reaction time:<br>20 sec |

In the course of these tests, it was noted that after agitation in the presence of blood, the hydroxide solutions remained clear while the solutions containing carbonate showed evidence of a gaseous release.

From table 1, one may note that it is the compositions containing sodium hydroxide or potassium hydroxide for an alkaline agent rather than sodium carbonate or potassium carbonate that render the best results in terms of emission of light intensities.

In the same way, one may note that these compositions, when sprayed on pure fresh blood or pure dried blood, will render the strongest light intensity.

Even though the results have not been reported in table 1, it was also noted that with the invention's compositions or with compositions used in the past containing potassium hydroxide, the emission of light happens in a sleeper flash noticeable during the dilution of the bloodspot, which led to the discarding of this alkaline agent.

Identical results were obtained with the compositions when vaporized on a bloodspot washed in water mixed with bleach, rinsed in water and dried off.

From table 1, one may further note that the preferred composition of the invention, in terms of the emission of light, both on fresh blood and on exposed blood dried for approximately 30 minutes, is a composition comprised of 5 mmoles/l of luminol, 90 mmoles/l of NaOH, and 50 mmoles/l of $H_2O_2$, diluted in water.

In fact, equally on fresh blood as on exposed and dried blood, the solution obtained with this preferred composition of the invention provokes an emission of very bright light that reaches a plateau when the concentration of NaOH is increased above 90 mmoles/l.

This composition is therefore particularly suitable for revealing traces of blood loss by wounded game animals, even under conditions of failing and fading light, for example, at sundown or under a full moon at night, as opposed to a night of complete darkness.

Nonetheless, such a composition has a pH higher than 12, which could be bothersome when it is used to detect and localise traces of blood at the scene of a crime or an accident, since at that pH reading, the identification of the DNA of the revealed blood might well be compromised.

In effect, at a pH higher or equal to 12, the blood localised by means of the luminol composition cannot, for the purpose of identification, be trusted to render reliable and reproducible DNA analyses.

In effect, it is to be noted that for a luminol composition at a pH higher or equal to 12, the DNA of the blood "treated" with the composition has become degraded.

In contrast, the invention's composition containing 5 mmoles/l of luminol, 50 mmoles/l of $H_2O_2$, and from 25 to 50 mmoles of NaOH, has a pH that is lowered to about 11.5, which allows reliable and reproducible DNA analyses, a fact which has been confirmed by the Institute of Criminal Investigations of the National Police (Institut de Recherche Criminelle de la Gendarmerie Nationale (IRCGN)).

Below a concentration of 25 mmoles/l of NaOH, the light intensity emitted by the compositions becomes approximately equivalent to the one obtained by the past compositions referred to.

Hence, in terms of an application in a criminal investigation, the invention's preferred composition is a composition containing 5 mmoles/l of luminol, 50 mmoles/l of hydrogen peroxide, and from 25 to 50 mmoles/l of NaOH, diluted in water, with a pH at the most equal to about 11.5.

In other words, the soda concentration is the one needed in order that the final solution's pH remain below 12. In fact, this needed soda concentration may vary in function of the type of receptacles used for the preparation of the pills, as will be described below, and which may modify the solution's pH, which in turn will require more or less soda in order to obtain a final pH that will remain below 12.

Another advantage of the invention's compositions is that they can be diluted in any aqueous environment that allows the solubility of the different components, with the exception of sea water and carbonated, gaseous water types, which tend to inhibit the reaction.

In that respect, the invention's compositions were tested diluted in lake water, river water, pond water, pool water, water spill, distilled water, tap water, without their exhibiting any loss of effectiveness.

It is understood that the invention's compositions should be used in the way of the past compositions, that is to say that their components ought to be diluted in water to be vaporized with a spray instrument on the sites where the search for traces of blood is being conducted.

This then signifies that the compositions are to be used in the form of a solution.

This solution may be prepared in advance and carried to the sites where the search for traces of blood is to be conducted. Likewise, it may be prepared on the spot itself, in which case it should be transported in separate receptacles, with each component in the composition in its solid form.

As the invention's compositions can be diluted in all types of non-carbonated fresh-water, a sufficient volume of this non-carbonated fresh-water can be carried along to the site to be investigated or, if present, such type of water may be secured from a source directly at the site itself.

In view of the above considerations, one other feature of the invention is a field kit useful for the preparation of a solution that will be sprayed on the search area and will allow the detection and localisation of traces of human or animal blood, this kit being as previously described or described in the subject claims hereinafter.

To be useful for hunting purposes, the invention's field kit preferably ought to contain the following components:

in a first receptacle, at least one individual dosage of 5 mmoles of luminol or of a luminol compound,
in a second receptacle, at least one individual dosage of 50 mmoles of hydrogen peroxide, and
in a third receptacle, at least one individual dosage of 90 mmoles of NaOH, or
in a receptacle, at least one individual dosage of about 5 mmoles of luminol or a luminol compound pre-mixed with either 90 mmoles of NaOH, or with 50 mmoles of $H_2O_2$, in a compatible solid state, and in a second receptacle, at least one individual dosage of either 50 mmoles of $H_2O_2$, or of 90 mmoles of soda;
or, finally, a pre-mixture in compatible form of these three components in a single receptacle.

In contrast, for an application that will be used in a search for traces of blood at the scene of a crime or an accident, and when the blood needs subsequently to be submitted to an DNA analysis, the invention's field kit should, preferably, contain the following components:

in a first receptacle, at least one individual dosage of 5 mmoles of luminol or of a luminol compound,
in a second receptacle, at least one individual dosage of 50 mmoles of hydrogen peroxide, and
in a third receptacle, at least one individual dosage of 25 to 50 mmoles of NaOH ; or
in a receptacle, at least one individual dosage of 5 mmoles of luminol or a luminol compound pre-mixed with 25 to 50 mmoles of NaOH, or 50 mmoles of $H_2O_2$, in a compatible solid state, and
in another receptacle, at least one individual dosage of at least 50 mmoles of $H_2O_2$, or of 25 to 50 mmoles of soda, depending on the pre-mixture in the first receptacle; or, finally,
a pre-mixture in compatible form of these three components in a single receptacle.

As previously pointed out, each receptacle may be a resealable vessel made of plastic or glass, or porcelain or whatever other substance. It could, for instance, be a pouch holding each component in the form of a powder.

Preferably, at least one receptacle—or all of the receptacles—should be formed by an alveolus fitted in at least one blister pack.

In this case, in a first variant, the field kit should contain at least one blister pack holding three alveoli, each of these alveoli holding a compound of the invention's composition.

In this case, the blister pack should contain in one of its alveoli the required individual dosage of luminol or a luminol compound, another of these alveoli should contain the required individual dosage of hydrogen peroxide, and the third alveolus should hold the required individual dosage of soda.

In a second variant, the invention's field kit should contain at least one blister pack with minimum two alveoli, one of these alveoli should contain the required individual dosage of luminol or of a luminol compound, pre-mixed with the required individual dosage of either soda or hydrogen peroxide in a compatible solid form, and the other of these two alveoli should contain the required individual dosage of either hydrogen peroxide or of soda, depending on the first pre-mix.

In these two variants, preferably, at least one of the categories of the individual dosages of luminol or of a luminol compound, or of a mixture of the latter with soda, or of hydrogen peroxide and soda should be in the form of a pill.

Nevertheless, preferably, in these two variants, each of the dosages should be in the form of a pill.

In a third variant, the field kit contains at least a blister pack with minimum one alveolus holding an individual dosage of a pre-mix formulation in a compatible solid form of the invention's three basic components. However, preferably in this variant, this individual dosage should be in the form of a pill.

In particular, but without limitation, when the individual dosages are in the form of pills, these may also contain excipients to facilitate the direct crushing of the pill in order to avoid a moist granulation due to the presence of NaOH (lactose, cellulose, calcium phosphate, etc.).

They may further contain any excipient known in the field (croscarmellose, Explotab® (sodium starch glycolate), etc.) that would facilitate the disintegration of the pill into an aqueous solvent.

To reconstitute the desired solution by means of, specifically, the invention's field kit, it is necessary to dilute in water or in an aqueous solvent an individual dosage of luminol or of a luminol compound or an individual dosage of a pre-mixture of the latter with either soda or hydrogen peroxide in a solid compatible form, and an individual dosage of either hydrogen peroxide or soda in keeping with the first pre-mixture. When the soda or the hydrogen peroxide are not of identical dosage to luminol or the luminol compound, an individual dosage of soda or of hydrogen peroxide is taken from the field kit's receptacles as per the invention's prescription. It is also possible to have a single pre-mixture of the invention's three components.

To search out and localise an animal that has been wounded or struck down under conditions of reduced visibility, one sprays the invention's composition, possibly taken from the invention's field kit, on the areas of the terrain where the animal is assumed to have passed, in order to produce a luminous reaction through the composition's contact with the blood traces left behind by the hunted animal.

The same procedure is used to search and localise traces of human blood at the scene of a crime or of an accident.

The invention is by no means restricted or limited to the modes of utilisation described and illustrated and which have been given merely by way of illustrative and non-exhaustive examples.

Hence, even though only luminol has been cited in the preceding examples, all of the luminol compounds can be used to the degree of their presence in sufficient quantity to provide measures of luminescence equivalent to those obtained through the use of luminol, in the way as defined in the invention. Examples of such luminol compounds are diethyl isoluminol and aminobutylethyl isoluminol.

This means that the invention comprises all the technical equivalents of the described modes as well as their combinations, provided these are carried out in keeping with the invention's requirements.

The invention claimed is:

1. Composition comprising:
   1-20 mmol/l of a luminol compound;
   25-100 mmol/l of hydrogen peroxide; and
   25-40 mmol/l of NaOH; and the composition having a pH which is lower than 11.5.

2. A field kit for the preparation of the composition as claimed in claim 1 wherein said kit comprises:
   a first receptacle including at least an individual dosage comprising the luminol compound in a quantity of between 1 and 20 mmoles in a pre-mixture with either said NaOH, or with 25 to 100 mmoles of said hydrogen peroxide, in a solid compatible form; and
   a second receptacle including at least an individual dosage comprising between 25 and 100 mmoles of the hydrogen peroxide, or said NaOH, corresponding to the pre-mixture in the first receptacle.

3. A field kit for the preparation of the composition as claimed in claim 1, wherein said kit comprises:
   a first receptacle including at least an individual dosage containing said luminol compound in a quantity sufficient to provide approximately 5 mmoles in a pre-mixture with said NaOH, or 50 mmoles of said hydrogen peroxide, in a solid compatible form, and
   a second receptacle including at least an individual dosage containing 50 mmoles of said hydrogen peroxide, or said NaOH, in accordance with the pre-mixture in the first receptacle.

4. A field kit for the preparation of the composition as claimed in claim 1, wherein said kit comprises:
   a first receptacle including at least an individual dosage containing said luminol compound in a quantity sufficient to provide approximately 5 mmoles in a mixture with 25 to 40 mmoles of said NaOH, or 50 mmoles of said hydrogen peroxide, in a solid compatible form, and
   a second receptacle including at least an individual dosage containing 50 mmoles of said hydrogen peroxide, or 25 to 40 mmoles of said NaOH.

5. A field kit for the preparation of the composition as claimed in claim 1, wherein the field kit contains at least one blister pack with a minimum of three alveoli, wherein at least one alveoli contains an individual dosage holding said luminol compound in a quantity sufficient to provide between 1 and 20 mmoles, and wherein at least one other alveoli contains an individual dosage holding between 25 and 40 mmoles of said NaOH, and wherein at least one other alveoli contains an individual dosage holding between 25 and 100 mmoles of said hydrogen peroxide.

6. A field kit for the preparation of the composition as claimed in claim 1, wherein said field kit contains either a blister pack and at least two alveoli, wherein at least one alveoli contains an individual dosage of said luminol compound in a quantity sufficient to provide between 1 and 20 mmoles in a pre-mixture with either said NaOH, in a quantity of between 25 and 40 mmoles, or with 25 to 100 mmoles of said hydrogen peroxide in solid compatible form; and at least one other alveoli contains an individual dosage with either a quantity of between 25 and 100 mmoles of said hydrogen peroxide, or of 25 to 40 mmoles of said NaOH depending on the first pre-mixture; or at least one blister pack containing at least one alveolus with a pre-mixture of the above-mentioned three basic components.

7. A field kit for the preparation of the composition as claimed in claim 1, comprising: the luminol, said hydrogen peroxide and the NaOH formulated in a single pre-mixture in formulations that allow their compatibility without generating a premature reaction, thus making it possible to enclose them jointly in one single receptacle.

8. A method of making a reconstitution of the composition as claimed in claim 1, wherein the reconstitution comprises diluting in water an individual dosage of said luminol compound, an individual dosage of said NaOH, or an individual dosage of a mixture of said luminol compound and said NaOH, and an individual dosage of the hydrogen peroxide.

9. The method of making a reconstitution as claimed in claim 8, wherein said individual doses are taken from receptacles of a kit.

10. Method for analyzing DNA of traces of blood at a scene of a crime comprising vaporizing the composition of claim 1 at said scene to produce reacted blood by a luminous reaction through contact of the composition with traces of blood, collecting the reacted blood to obtain collected blood and DNA analyzing the collected blood.

* * * * *